US012599565B2

(12) United States Patent
Penhasi et al.

(10) Patent No.: US 12,599,565 B2
(45) Date of Patent: Apr. 14, 2026

(54) STABLE BENZIMIDAZOLE FORMULATION

(71) Applicant: DEXCEL PHARMA TECHNOLOGIES LTD., Jerusalem (IL)

(72) Inventors: Adel Penhasi, Holon (IL); Avi Avramoff, Haifa (IL); Maxim Gomberg, Jerusalem (IL); Valerie Azoulay, Pardes Hana (IL)

(73) Assignee: DEXCEL PHARMA TECHNOLOGIES LTD., Jerusalem (IL)

( * ) Notice: Subject to any disclaimer, the term of this patent is extended or adjusted under 35 U.S.C. 154(b) by 271 days.

(21) Appl. No.: 17/501,237

(22) Filed: Oct. 14, 2021

(65) Prior Publication Data

US 2022/0031622 A1 Feb. 3, 2022

Related U.S. Application Data

(63) Continuation of application No. 14/053,611, filed on Oct. 15, 2013, now abandoned, which is a continuation of application No. 12/866,255, filed as application No. PCT/IL2009/000467 on May 5, 2009, now abandoned.

(60) Provisional application No. 61/071,557, filed on May 6, 2008.

(51) Int. Cl.
| | |
|---|---|
| *A61K 9/20* | (2006.01) |
| *A61K 9/16* | (2006.01) |
| *A61K 9/28* | (2006.01) |
| *A61K 9/50* | (2006.01) |
| *A61K 31/4439* | (2006.01) |

(52) U.S. Cl.
CPC ............ *A61K 9/2095* (2013.01); *A61K 9/282* (2013.01); *A61K 9/2866* (2013.01); *A61K 31/4439* (2013.01); *A61K 9/1676* (2013.01); *A61K 9/5042* (2013.01)

(58) Field of Classification Search
None
See application file for complete search history.

(56) References Cited

U.S. PATENT DOCUMENTS

| | | | |
|---|---|---|---|
| 3,634,271 A | 1/1972 | Friedman | |
| 4,017,647 A | 4/1977 | Ohno et al. | |
| 4,786,505 A | 11/1988 | Lovgren et al. | |
| 4,853,230 A | 8/1989 | Lovgren et al. | |
| 4,888,367 A | 12/1989 | Quigley et al. | |
| 5,045,321 A | 9/1991 | Makino et al. | |
| 5,093,132 A | 3/1992 | Makino et al. | |
| 5,225,202 A | 7/1993 | Hodges et al. | |
| 5,232,706 A | 8/1993 | Palomo Coll | |
| 5,330,982 A | 7/1994 | Tyers | |
| 5,376,385 A | 12/1994 | Barton et al. | |
| 5,433,959 A | 7/1995 | Makino et al. | |
| 5,508,276 A | 4/1996 | Anderson | |
| 5,536,735 A | 7/1996 | Takechi et al. | |
| 5,639,478 A | 6/1997 | Makino | |
| 5,690,960 A * | 11/1997 | Bengtsson | A61P 1/04 |
| | | | 424/494 |
| 5,753,265 A | 5/1998 | Bergstrand | |
| 5,817,338 A | 10/1998 | Bergstrand | |
| 5,879,708 A | 3/1999 | Makino et al. | |
| 6,013,281 A | 1/2000 | Lundberg | |
| 6,017,560 A | 1/2000 | Makino et al. | |
| 6,077,541 A | 6/2000 | Chen et al. | |
| 6,096,340 A | 8/2000 | Chen et al. | |
| 6,123,962 A | 9/2000 | Makino et al. | |
| 6,149,942 A | 11/2000 | Scheiwe | |
| 6,174,548 B1 | 1/2001 | Chen et al. | |
| 6,228,400 B1 | 5/2001 | Lee et al. | |
| 6,245,351 B1 | 6/2001 | Nara et al. | |
| 6,262,085 B1 | 7/2001 | Whittle | |
| 6,268,385 B1 | 7/2001 | Whittle | |
| 6,296,875 B1 | 10/2001 | Makino et al. | |
| 6,326,384 B1 | 12/2001 | Whittle | |
| 6,380,234 B1 | 4/2002 | Makino | |
| 6,521,256 B2 | 2/2003 | Makino | |
| 6,602,522 B1 | 8/2003 | Chen | |
| 6,623,752 B1 | 9/2003 | Fischer et al. | |
| 6,623,759 B2 | 9/2003 | Heese | |
| 6,699,885 B2 | 3/2004 | Phillips | |
| 6,726,927 B2 | 4/2004 | Chen | |
| 6,733,778 B1 | 5/2004 | Chen | |
| 6,749,864 B2 | 6/2004 | Makino | |

(Continued)

FOREIGN PATENT DOCUMENTS

| | | |
|---|---|---|
| DE | 19626045 | 12/1998 |
| EP | 0005129 B1 | 4/1981 |

(Continued)

OTHER PUBLICATIONS

What is pH and how is it measured? (2003).*
Important Biological Buffers.*
Gilbar "A Guide to Enteral Drug Administration in Palliative Care". Mar. 1999.*
PH Adjusting Database Jun. 2007.*
Ansel, Howard C., et al., "*Pharmaceutical Dosage Forms and Drug Delivery Systems*", Williams & Wilkins, 6th ed., (1995), (35p).

(Continued)

*Primary Examiner* — Danah Al-Awadi

(74) *Attorney, Agent, or Firm* — Allan A. Fanucci, Esq.

(57) ABSTRACT

An omeprazole delayed release tablet comprises a core and an enteric coating over the core. The core consists essentially of omeprazole, lactose, sodium starch glycolate, sodium stearate, and sodium stearyl fumarate. The enteric coating over the core consists essentially of hydroxypropyl methyl cellulose (HPMC) acetate succinate, triethyl citrate, sodium lauryl sulfate, talc, monoethanol amine, and less than 500 ppm of residual ammonium hydroxide.

13 Claims, 6 Drawing Sheets

(56) References Cited

U.S. PATENT DOCUMENTS

| | | | |
|---|---|---|---|
| 6,780,435 B2 | 8/2004 | Chen | |
| 6,855,336 B2 | 2/2005 | Chen | |
| 7,988,999 B2 | 8/2011 | Dietrich et al. | |
| 9,023,391 B2 | 5/2015 | Lahav et al. | |
| 2002/0039597 A1 | 4/2002 | Ukai | |
| 2002/0054913 A1 | 5/2002 | Heese | |
| 2002/0098242 A1 | 7/2002 | Darder | |
| 2002/0128293 A1 | 9/2002 | Knopfler | |
| 2002/0160046 A1 | 10/2002 | Robinson | |
| 2003/0021844 A1 | 1/2003 | Barthelemy et al. | |
| 2003/0064107 A1* | 4/2003 | Yu | A61P 31/00 |
| | | | 424/494 |
| 2003/0091643 A1 | 5/2003 | Friesen | |
| 2003/0175348 A1 | 9/2003 | Kofler | |
| 2003/0228363 A1* | 12/2003 | Patel | A61K 9/2866 |
| | | | 424/471 |
| 2003/0236285 A1 | 12/2003 | Patel | |
| 2004/0028737 A1 | 2/2004 | Ceshpande | |
| 2004/0175427 A1 | 9/2004 | Chen | |
| 2004/0209919 A1 | 10/2004 | Makino | |
| 2004/0213847 A1 | 10/2004 | Matharu | |
| 2005/0163846 A1 | 7/2005 | Aoki | |
| 2006/0003005 A1* | 1/2006 | Cao | A61K 31/545 |
| | | | 514/192 |
| 2006/0093680 A1* | 5/2006 | Humar | A61K 9/2009 |
| | | | 424/490 |
| 2006/0159762 A1 | 7/2006 | Stanic Ljubin et al. | |
| 2006/0165778 A1 | 7/2006 | Hassan | |
| 2006/0204577 A1 | 9/2006 | Crew et al. | |
| 2007/0065513 A1* | 3/2007 | Avramoff | A61K 9/5078 |
| | | | 424/470 |
| 2007/0196485 A1* | 8/2007 | Lahav | A61K 9/0053 |
| | | | 424/472 |
| 2007/0243250 A1* | 10/2007 | Heinicke | A61K 31/00 |
| | | | 424/465 |
| 2008/0131467 A1* | 6/2008 | Nelson | A61K 9/2866 |
| | | | 514/777 |
| 2008/0161364 A1 | 7/2008 | Tatsumi et al. | |
| 2009/0175935 A1* | 7/2009 | Setty | A61P 13/00 |
| | | | 427/2.21 |
| 2009/0297441 A1 | 12/2009 | Canham et al. | |
| 2010/0183710 A1 | 7/2010 | Bolugoddu | |
| 2010/0297226 A1* | 11/2010 | Penhasi | A61K 9/2077 |
| | | | 424/478 |

FOREIGN PATENT DOCUMENTS

| | | | |
|---|---|---|---|
| EP | 0124495 B1 | 1/1987 | |
| EP | 237200 B1 | 7/1992 | |
| EP | 519144 B1 | 8/1997 | |
| FR | 2692146 A1 | 6/1992 | |
| GB | 2189698 A | 11/1987 | |
| WO | WO 83/00435 A1 | 2/1983 | |
| WO | WO 96/24338 | 8/1996 | |
| WO | WO 96/37195 | 11/1996 | |
| WO | WO 97/12581 | 4/1997 | |
| WO | WO 98/00114 | 1/1998 | |
| WO | WO 98/40069 | 9/1998 | |
| WO | WO 98/50019 | 11/1998 | |
| WO | WO 99/25323 | 5/1999 | |
| WO | WO 99/27917 | 6/1999 | |
| WO | WO 00/12064 | 3/2000 | |
| WO | WO 00/50038 | 8/2000 | |
| WO | WO 00/78284 A1 | 12/2000 | |
| WO | WO 01/24777 | 4/2001 | |
| WO | WO 02/11699 | 2/2002 | |
| WO | WO 02/19991 | 3/2002 | |
| WO | WO 02/102356 | 12/2002 | |
| WO | WO 03/024449 | 3/2003 | |
| WO | WO 03/072087 | 9/2003 | |
| WO | WO 03/077888 | 9/2003 | |
| WO | WO 03/103638 | 12/2003 | |
| WO | WO 04/000279 A1 | 12/2003 | |
| WO | WO 04/014345 | 2/2004 | |
| WO | WO 04/050058 | 6/2004 | |
| WO | WO 04/050068 | 6/2004 | |
| WO | WO 04/089333 | 10/2004 | |

OTHER PUBLICATIONS

Ansel, Howard C., et al., "*Pharmaceutical Dosage Forms and Drug Delivery Systems*", Lippinscott Williams & Wilkins, 7th ed. (1999), (38p).

Dexcel Responses to DRL Invalidity Contentions (redacted) dated May 9, 2016, (236p).

Dexcel Responses to SUN's Invalidity Contentions (redacted) dated May 20, 2016, (138p).

DRL Invalidity Contentions (redacted) dated Mar. 17, 2016 (65p).

SUN Invalidity Contentions (redacted) dated Apr. 5, 2016 (42p).

Bloor, J.R., et al., "*The In Vitro and In Vivo Performance of Aqueous Based Enteric Coats of Neutralized Hydroxypropyl Methyl Cellulose Phthalate*", Drug Development and Industrial Pharmacy vol. 15, (1989), pp. 2227-2243.

Borukhov, Itmar et al., "Polyelectrolyte Titration: Theory and Experiment," May 2000, https://arxiv.org/pdf/cond-mat/0005306.pdf. (13p).

Clinical Pharmacology and Biopharmaceutics Review New Drug Application, Center For Drug Evaluation and Research, OCPB Review, Cymbalta® (Duloxetine HCl) EC-Capsules; C:/dmautop/temp/21427 Review Final.doc, last printed Aug. 23, 2002, (63p).

Eudragit® L30D-55, Specification and Test Methods, Evonik Industries AG, May 2014 (8p).

Handbook of Granulation Technology, http://www.gmpua.com/Process/Tablet/Granulation/Granulation Technology, Taylor & Francis Group, LLC (2005), 624 pages.

Heinamaki, J.T., et al., "*Comparative Evaluation of Ammoniated Aqueous and Organic-Solvent-Based Cellulose Ester Enteric Coating Systems: A Study on Free Films*", Int. J. Pharmaceutics Elsevier BV NL. vol. 109(1), pp. 9-16.

Hilton, A.K. et al., "*Use of Hydroxypropyl Methylcellulose Acetate Succinate in an Enteric Polymer Matrix to Design Controlled-Release Tablets of Amoxicillin Trihydrate*," J. Pharm. Science, vol. 82(7), (1993), pp. 737-743.

Important Biological Buffers, Google date Oct. 25, 2007, http://staff.ustc.edu.cn/liuyz/methods/buffer.htm, Aug. 31, 2015. (2p).

Kohlmann, Frederick J., "*What is Ph, And How Is It Measured?*" A technical handbook For Industry—GLI International—Hach Company (2003), 24p.

Lin, Feng-Chih, et al., "*The Dissolution Kinetics of Brucite Antigorite Talc and Phlogopite at Room Temperature and Pressure,*" American Mineralogist, vol. 66, (1981), pp. 801-806.

Palaniswamy, R., et al., "Association Behavior of Poly(methacrylic acid)-block-Poly(methylmethacrylate) in Aqueous Medium: Potentiometric and Laser Light Scattering Studies," (8p).

Pilbrant, A., et al., "*Development of an Oral Formulation of Omeprazole*," Scand. J. Gastroenterol. vol. 20, (1985), pp. 113-120.

Rudnic, Edward et al., "*Oral Solid Dosage Forms*", Remington: The Science and Practice of Pharmacy 19th ed., Mack Publishing Company (1995), (47p).

Stafford, J.W., et al., "*Enteric Film Coating Using Completely Aqueous Dissolved Hydroxypropyl Methyl Cellulose Phthalate Spray Solutions*," Drug Development and Industrial Pharmacy, vol. 8 (1982), pp. 513-530.

Subburayalu, Raja et al., "*Effects of pH of Enteric Polyer on Dissolution Profile of Duloxetine HCl Delayed Release Pellets at Various pH Ranges*" IJPSR, 2013, pp. 3400-3407.

"Talc" retrieved from internet (rruff.geo.arizona.edu/doclib/hom/talc.pdf) on Jul. 27, 2006.

International Search Report to PCT Application No. PCT/IL00/00364, dated Oct. 24, 2000 (1 p).

International Preliminary Examination Report to PCT Application No. PCT/IL00/00364, dated Sep. 17, 2001 (4p).

Search Report to European Application EP1187599 dated Apr. 30, 2004.

Office Action to European Application EP20090742569 dated Aug. 18, 2011.

(56)     References Cited

OTHER PUBLICATIONS

Office Action to European Application EP1187599 dated Mar. 22, 2005.
Office Action to European Application EP1187599 dated Aug. 8, 2006.
Office Action to European Application EP1187599 dated Apr. 23, 2007.
Office Action to Israel Application IL208925 dated Dec. 19, 2012.
Important Biological Buffers. Oct. 25, 2007.

* cited by examiner

STABLE BENZIMIDAZOLE FORMULATION

This application is a continuation of U.S. patent application Ser. No. 14/053,611, filed Oct. 15, 2013, which is a continuation of U.S. patent application Ser. No. 12/866,255, filed Nov. 3, 2010, now abandoned, which is a national phase application of PCT/IL2009/000467, filed May 5, 2009, which claims priority to U.S. Provisional Patent Application Ser. No. 61/071,557, filed May 6, 2008, the entireties of all of which are incorporated herein by reference.

FIELD OF THE INVENTION

The present invention relates to a novel stable formulation for an acid labile benzimidazole, and methods of preparation and administration thereof, and in particular, for a stable formulation of a benzimidazole which is suitable for oral administration, and has low levels of residual volatile excipients such as solvents.

BACKGROUND OF THE INVENTION

Omeprazole, Pantoprazole, Lansoprazole and other derivatives of benzimidazole, which are active proton pump inhibitors and used conventionally for decreasing gastric secretion are known to be susceptible to degradation and transformation in acid media. Omeprazole, 5-methoxy-2 (((4-methoxy-3,5-dimethyl-2-pyridinyl)methyl)sulfinyl)-1H-benzimidazole, is disclosed and described in European Patent No. 5129 and European Patent No. 124495, as well as in numerous other patents and published patent applications.

The susceptibility of these active proton pump inhibitor substances to degradation and transformation in acid media increases the difficulty of preparing a pharmaceutical form designed for oral administration. If the active substance comes into contact with the stomach content, which is a highly acidic medium, these chemical substances become degraded. Thus, these benzimidazole derivatives should be protected both during storage and during their passage through the acidic environment of the stomach.

The stability of Omeprazole has been extensively studied (see for example A. Pilbrant and C. Cederberg, *Scan. J. Gastroenterol.*, 20: 113-120, 1985). Omeprazole degrades with a half-life of less than 10 minutes in an environment with pH values below 4.0. At pH 6.5, the half life of Omeprazole is 18 hours and at pH 11 about 300 days. Therefore, the environment of Omeprazole should be kept at a sufficiently high pH value in order to maintain the stability of the compound, in a formulation which is suitable as a product for oral administration, for example by locating Omeprazole within a core which also contains alkaline constituents. This leads to an alkaline reaction aimed at improving stability of the active substance during manufacture thereof and during storage of the pharmaceutical formulation.

In addition, such a formulation must protect Omeprazole from the acidic environment of the stomach, since if Omeprazole is given orally without any protective coating, it will degrade in the acid environment of the stomach. European Patent No. 237,200 discloses one solution, which is to directly coat the solid core containing Omeprazole, or another benzimidazole derivative, with an enteric coating layer.

However, this apparent solution to the instability of Omeprazole caused further complications, in that the alkaline core containing Omeprazole was found to react with the enteric coating, thereby causing the enteric coating to degrade. A solution to these further complications is disclosed in United Kingdom Patent Application No. 2,189, 698, in which Omeprazole is contained within a solid active core, which is coated first with a subcoating layer and then with an enteric coating layer. The enteric coating layer protects the Omeprazole during the passage through the stomach, while the subcoating layer protects the enteric coating layer from reacting negatively with the alkaline core containing Omeprazole.

The background art describes other attempts to provide formulations which are suitable for oral administration of acid-labile substances. For example, PCT Application No. WO 97/12581 discloses a composition adapted for oral administration containing Omeprazole which specifically does not include alkaline-reacting compounds. Instead, the composition features a core composed of a nuclei and Omeprazole compressed together, an intermediate layer and an enteric layer.

European Patent Application No. 519,144 discloses a formulation for Omeprazole, which features a neutral (sugar) core. Omeprazole is sprayed onto the sugar core, after which an intermediate coating layer and an enteric coating layer are sprayed onto the core.

PCT Application No. WO 98/00114 discloses a modification to other background art formulations for Omeprazole, in which the intermediate subcoating layer is partially neutralized with an alkaline compound. However, this modified formulation still features the subcoating layer, which is a disadvantage in that it complicates the manufacturing process and increases the expense and difficulty of manufacture. Thus, the formulation disclosed in PCT Application No. WO 98/00114, like those disclosed in European Patent Application No. 519,144 and other background art references, has the disadvantage of requiring the intermediate layer.

PCT Application No. WO 83/00435 discloses a solid dosage form, such as a capsule or tablet, containing a pharmacologically active agent coated with an anionic polymer, which is insoluble in gastric juice and in intestinal juice below pH 7. The preferred anionic polymer is a partly methyl esterified methacrylic acid polymer in which the ratio of free carboxylic groups to ester groups is about 1:2. In contrast to the present invention, Omeprazole is not disclosed as one of the active agents.

French Application No. 2,692,146 discloses stable compositions of microgranules of gastro-protected Omeprazole. The composition features a center of Omeprazole diluted in mannitol. This center is coated with an intermediate layer featuring mannitol. An enteric coating is then added over this intermediate layer. PCT Application No. WO 97/12581 discloses a formulation in which an intermediate layer between the core and an enteric coating contains silicium dioxide.

PCT Application No. WO 96/37195 discloses a formulation which lacks a subcoating layer, but which features a core containing titanium dioxide. Both the core containing Omeprazole and the enteric coating layer placed on top of the core include titanium dioxide as an ingredient. Unfortunately, titanium dioxide is only able to mask the discoloration caused by the reaction between Omeprazole and the enteric coating layer, but cannot prevent such an undesirable reaction. Thus, the disclosed formulation does not prevent the undesirable reaction between the benzimidazole derivative and the enteric coating, which is known in the art.

German Patent Application No. 196 26 045 A1 discloses a method for stabilising Omeprazole by coating small tablets or pellets, containing large amounts of mannitol, with a subcoating of Eudragit L. The subcoating of Eudragit L is neutralized, after which a final enteric coat of non-neutralized Eudragit L is applied.

A formulation of a benzimidazole derivative, such as Omeprazole, which lacks an intermediate coating layer and yet which is stable both during storage and during the passage through the stomach, is described in U.S. patent application Ser. No. 10/018,992. This formulation involves neutralization of the enteric coating with an alkaline compound, such as ammonium hydroxide. The formulation is simple to manufacture and exposes the sensitive benzimidazole derivative to fewer production steps, thereby decreasing degradation of the active compound during production. However, neutralization of enteric coatings with an alkalinizing agent usually results in a certain amount of the alkalinizing agent remaining in the final product. Furthermore, benzimidazole formulations are frequently prepared using volatile organic solvents, a residual amount of which is also found in the final product. Since there is no therapeutic benefit from residual alkalinizing agents and residual solvents, and these may, in fact, have a harmful effect, it is desirable to keep the levels of such residual solvents as low as possible for toxicity/safety reasons.

SUMMARY OF THE INVENTION

The background art does not teach or suggest a benzimidazole formulation, particularly for Omeprazole, which lacks an intermediate layer and yet which is stable both during storage and during the passage through the stomach, and which has low levels of residual alkalinizing agents and residual solvents.

The present invention overcomes these drawbacks of the background art by providing a benzimidazole formulation which lacks an intermediate layer and yet which is stable both during storage and during the passage through the stomach, and which has low levels of residual volatile excipients, including but not limited to residual alkalinizing agents and/or residual solvents.

According to some embodiments of the present invention, there is provided a stable composition for a benzimidazole derivative, the composition comprising a substrate, comprising the benzimidazole derivative; and a single coating layer consisting essentially of at least one neutralized enteric polymer, the enteric polymer having been neutralized by an alkalizing agent. The alkalizing agent is selected from the group consisting of amino alcohols, alkylene diamines, ammonia solution, arginine and lysine. Optionally and preferably there is a single coating layer layered directly over the substrate, without an intermediate layer between the substrate and the enteric coating. The composition comprises less than about 500 parts per million of residual alkalizing agent relative to the total weight of the composition.

According to some embodiments of the present invention, there is provided a stable composition for a benzimidazole derivative, the composition comprising a substrate comprising the benzimidazole derivative and a single coating layer consisting of one or more enteric polymers treated by at least one volatile alkalizing agent prior to applying over the substrate. The composition comprises less than 500 parts per million of residual volatile alkalizing agents relative to the composition weight, and a pH of the coating layer is in the range of from about 4.5 to about 6.5 as measured in 30 ml of distilled water at 20-25° C.

Optionally and preferably, the pH is in the range of from about 5 to about 6; more preferably the pH is about 5.

Optionally and preferably, the alkalizing agent comprises at least one of basic sodium, potassium, methanolamine, ammonium solution (such as ammonium hydroxide), amino alcohols (such as methanolamine, monoethanol amine, or propanolamine, or combinations thereof), arginine, lysine, and alkylene diamines (such as methylene diamine, ethylene diamine, or propylene diamine, or combinations thereof).

Optionally and preferably, the enteric polymer is dissolved in an organic solvent prior to application. Optionally and preferably, such a composition comprises less than about 1000 parts per million of residual organic solvent.

Non-limiting examples of organic solvents include acetone, ethanol, isopropanol or a mixture thereof.

Non-limiting examples of enteric polymers include cellulose acetate phthalate (CAP); hydroxypropyl methylcellulose phthalate (HPMCP); polyvinyl acetate phthalate; cellulose acetate trimellitate; poly((methacrylic acid, methyl methacrylate)1:1) (Eudragit L100™), poly((methacrylic acid, ethyl acrylate)1:1) (Eudragit L30D-55) or Eudragit L100-55™, (poly(methacrylic acid, methyl methacrylate)1: 2) Eudragit™ S hydroxypropyl methylcellulose acetate succinate (HPMCAS), sodium alginate, and alginic acid or mixtures thereof.

Optionally and preferably, the substrate is an active core for containing the benzimidazole derivative, such as, for example, a pellet, a bead or a tablet.

Optionally and preferably, the active core is a tablet formed by compression.

According to some embodiments of the present invention, the substrate features a neutral core; and an active coating containing the benzimidazole derivative, wherein the active coating is layered over the neutral core; such that the composition is in a form of a pellet.

Optionally and preferably, the substrate features a core containing the benzimidazole derivative with a suitable binding agent, the core being prepared by spheronisation and pelletization; such that the composition is in a form of a pellet.

The benzimidazole is optionally one or more of Omeprazole, Pantoprazole, Lansoprazole, Leminoprazole, Perprazole, Rabeprazole, or pharmaceutically acceptable salts thereof, or combinations thereof.

Optionally, the substrate further comprises a filler, such as, for example, one or more of microcrystalline cellulose, sodium carboxymethycellulose, ethylcellulose, cellulose acetate, starch, lactose, glucose, fructose, sucrose, dicalcium phosphate, sorbitol, mannitol, mantitol, lactitol, xylitol, isomalt, erythritol, and hydrogenated starch hydrolysates, or a mixture thereof.

Optionally, the substrate further comprises a disintegrant, such as, for example, one or more of low-substituted carboxymethyl cellulose sodium, cross-linked polyvinyl pyrrolidone, sodium starch glycolate, cross-linked sodium carboxymethyl cellulose, pregelatinized starch, microcrystalline starch, water insoluble starch, calcium carboxymethyl cellulose, and low substituted hydroxypropyl cellulose magnesium aluminum silicate, or a mixture thereof.

Optionally, the substrate further comprises a lubricant, such as, for example, one or more of sodium stearyl fumarate, polyethylene glycol, silica colloidal anhydrous and magnesium stearate, or a mixture thereof.

Optionally, the substrate further comprises an alkalinizing aunt, such as, for example, one or more of sodium stearate, meglumine, disodium phosphate, and ammonia, or a mixture thereof.

Optionally, the coating layer further comprises a plasticizer, such as, for example, one or more of a citric acid ester and a phthalic acid ester.

Optionally, the coating layer further comprises a surfactant, such as, for example, one or more of polysorbate 80 and sodium lauryl sulfate.

Optionally, the coating layer further comprises a glidant, such as, for example one or more of talc and titanium dioxide.

Optionally, the coating layer further comprises at least one of a coloring agent and a polishing agent.

According to some embodiments there is provided a method for preparing a stable composition for a benzimidazole derivative, the method comprising neutralizing one or more enteric polymers with at least one volatile alkalizing agent; and layering the enteric polymer(s) over a substrate comprising the benzimidazole derivative to form a coating layer, the composition comprising the substrate and the coating layer, such that the composition comprises less than 1000 parts per million of residual volatile alkalizing agents relative to composition weight.

Optionally, the alkalizing agent comprises one or more of amino alcohols, alkylene diamines, arginine, lysine, and ammonia solution.

According to some embodiments, there is provide a method for preparing a stable composition for a benzimidazole derivative, the method comprising dissolving one or more enteric polymers in an organic solvent; neutralizing the enteric polymer(s) with at least one volatile alkalizing agent; and layering the enteric polymer(s) over a substrate comprising the benzimidazole derivative to form a coating layer, the composition comprising the substrate and the coating layer, such that the composition comprises less than 1000 parts per million of residual solvent relative to composition weight.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
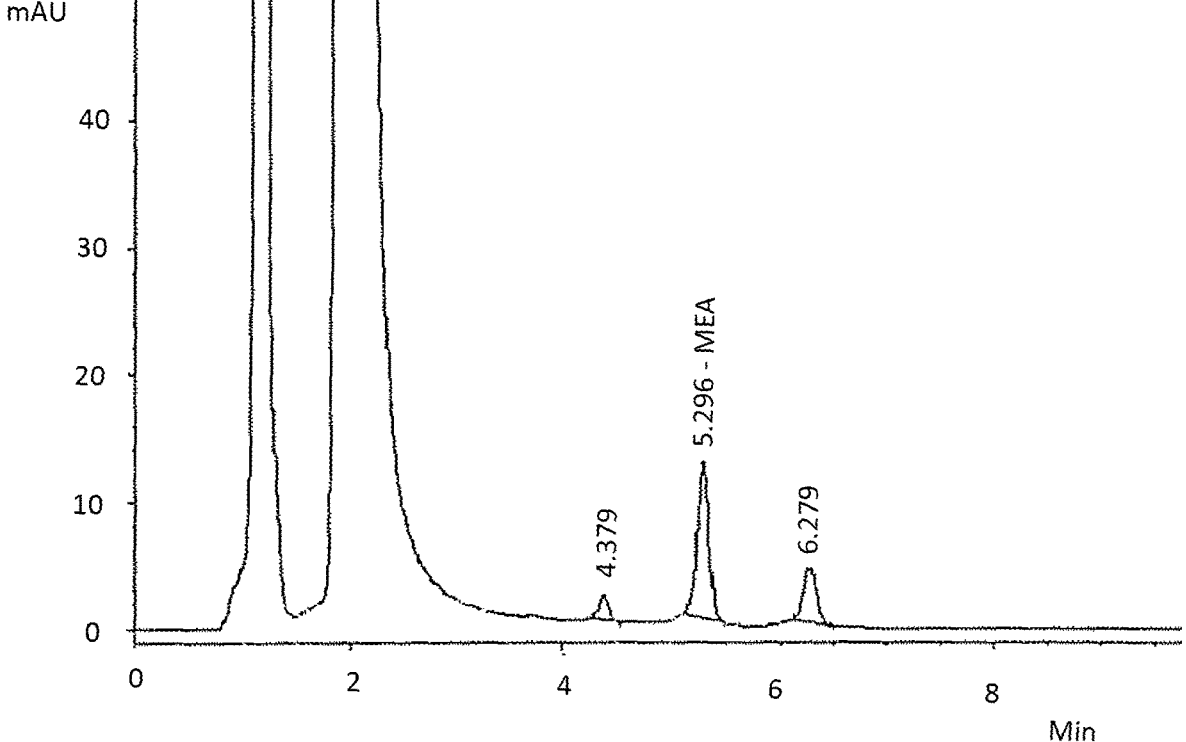
FIGS. 1-6 relate to the suitability of test method for determination of residual monoethanolamine.
Figure 2:
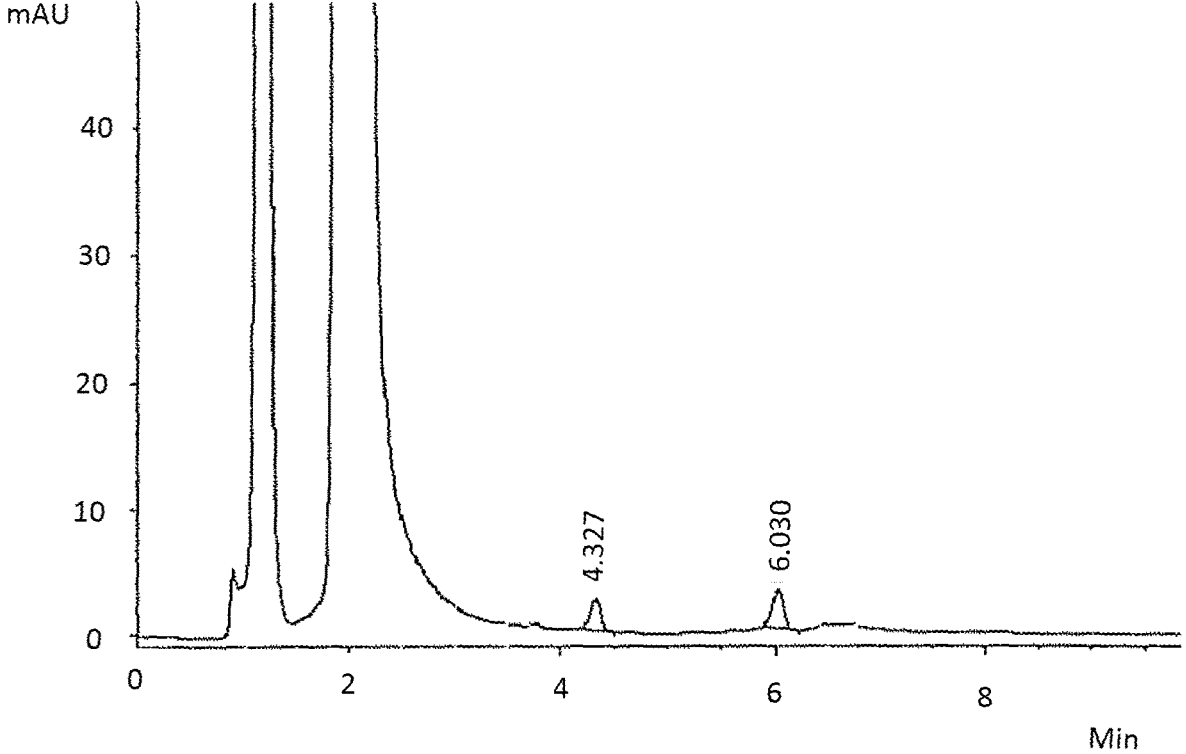
Figure 3:
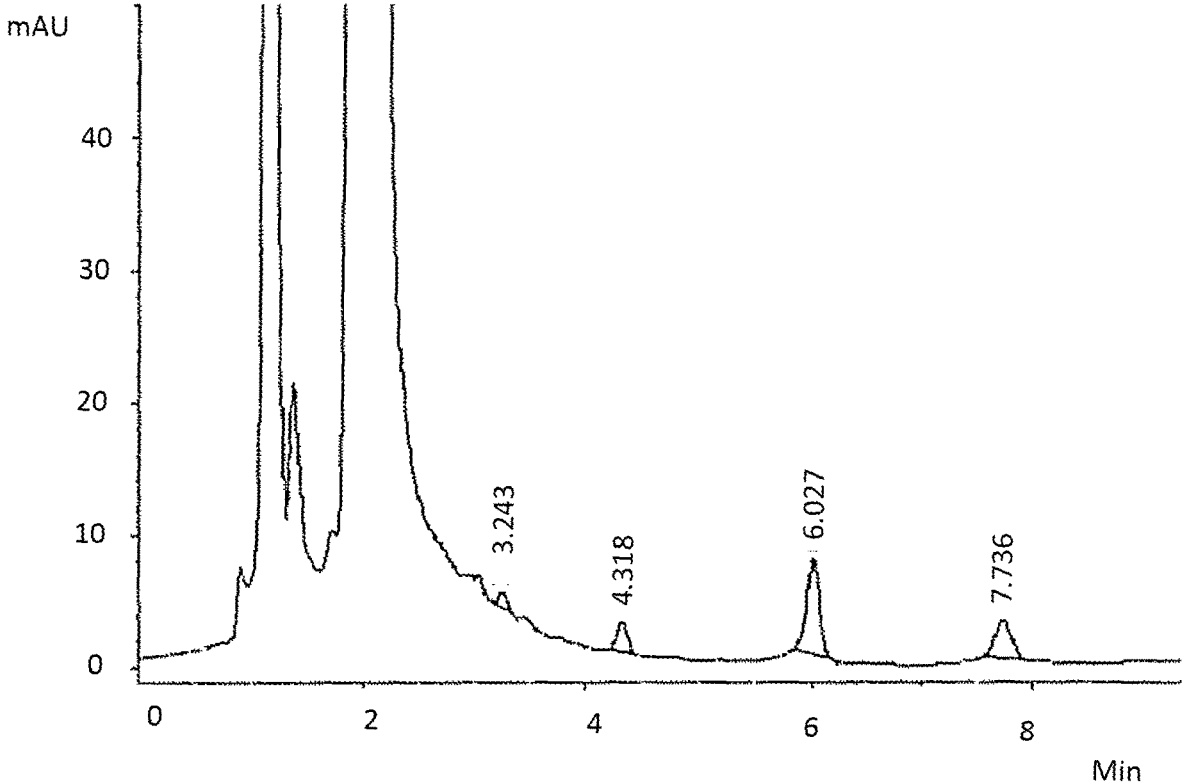
Figure 4:
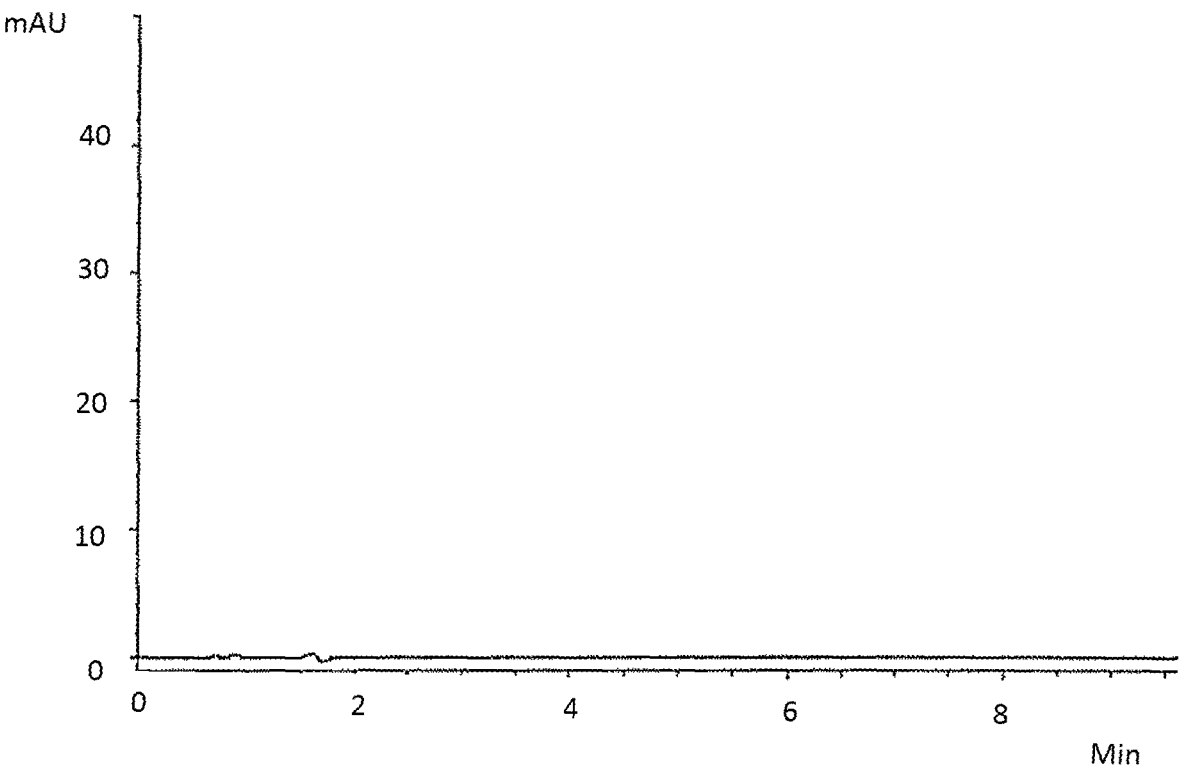

The formulation of the present invention contains a benzimidazole derivative, such as Omeprazole, and is able to maintain the stability of this active ingredient without a separating layer between the active compound and an enteric coating layer. Instead, the enteric coating layer is prepared as an aqueous dispersion or in organic solvent and neutralized with an alkalinizing agent, before being applied as a solution directly to the benzimidazole derivative substrate.

Preferably, the aqueous dispersion has a pH in the range of at least 6.5, and more preferably in the range of from about 7 to about 10.

After being applied to the substrate, the aqueous dispersion dries to form a coating layer, preferably having a pH in the range of from about 4.5 to about 6.5, and more preferably from about 5 to about 6, as measured in 30 ml of distilled water at 22° C.

The resulting formulation comprises less than about 500 parts per million of residual alkalizing agent relative to the total weight of the composition.

Preferably, the composition comprises less than about 1000 parts per million of residual organic solvent and more preferably less than about 500 ppm.

The resultant formulation maintains the stability of the benzimidazole derivative during storage and at the same time protects the product during passage through the acidic environment of the stomach. The problem of interaction between the enteric coat and the alkaline core is thus completely eliminated as the enteric coat at this stage does not release the free protons that are responsible for its acidic properties. At the same time, the formulation has low levels of residual alkalinizing agent and residual organic solvent in the final product.

The preparation of the benzimidazole-containing compositions of the present invention is described first with reference to the following general description and then with reference to the following non-limiting examples of the preparation and application of the compositions of the present invention.

The formulation of the present invention includes a substrate which features the benzimidazole derivative. A coating suspension, which has a pH value of at least 6.5 and more preferably of from about 7 to about 10, is prepared with the enteric coating material. Preferably, a pH value in the desired range is obtained by adding an alkalinizing agent to an enteric coating material More preferably, the alkalinizing agent is selected from the group consisting of basic sodium, potassium, methanolamine or ammonium hydroxide, amino alcohols and alkylene diamines, arginine, and lysine. This enteric coating solution is then layered directly over the substrate to form the composition of the present invention.

The term "substrate" refers to substantially any structure which features the benzimidazole derivative, such as Omeprazole. For example, this structure could be an active core containing the benzimidazole derivative. The active core may comprise, for example, a pellet, a bead, or a tablet. This active core could be prepared in a number of different ways which are known in the art. For example, the active core could be formed by compressing the benzimidazole derivative with an alkaline substance. As another example, the active core could be prepared by mixing the benzimidazole derivative with an alkaline substance, spheronizing the mixture and then forming cores through pelletisation. As yet another example, the active core is optionally and preferably prepared by embedding the active ingredient in a poloxamer and compressing the embedded material into tablets. The active core is also optionally formed by granulating the active ingredient with an alkaline substance and compressing the granulation into tablets.

Alternatively and optionally, the structure could include a neutral core, such as a sugar bead which does not contain the benzimidazole derivative, over which the benzimidazole derivative is coated. The coating includes Omeprazole or other benzimidazole derivative with a suitable adhesive polymer. The pellet may optionally be prepared by spheronization and pelletization of the benzimidazole derivative and a suitable binding agent.

The benzimidazole derivative of the present invention may comprise, for example, Omeprazole, Pantoprazole, Lansoprazole, Leminoprazole, Perprazole, or Rabeprazole, or pharmaceutically acceptable salts thereof. Preferably, the benzimidazole derivative is omeprazole.

Optionally, the substrate may further comprise a filler. Examples of suitable fillers include microcrystalline cellulose, sodium carboxymethycellulose, ethylcellulose, cellulose acetate, starch, lactose, glucose, fructose, sucrose, dicalcium phosphate, sorbitol, manitol, mantitol, lactitol, xylitol, isomalt, erythritol, and hydrogenated starch hydrolysates, or a mixture thereof.

Further optionally, the substrate may comprise a disintegrant, such as, for example, low-substituted carboxymethyl cellulose sodium, cross-linked polyvinyl pyrrolidone, sodium starch glycolate, cross-linked sodium carboxymethyl cellulose, pregelatinized starch, microcrystalline starch, water insoluble starch, calcium carboxymethyl cellulose, and low substituted hydroxypropyl cellulose magnesium aluminum silicate, or a mixture thereof.

Also optionally, the substrate may further comprise a lubricant, such as, for example, sodium stearyl fumarate, polyethylene glycol, silica colloidal anhydrous and magnesium stearate, or a mixture thereof.

The substrate may optionally further comprise an alkalinizing agent, such as, for example, sodium stearate, meglumine, disodium phosphate, magnesium carbonate, and ammonia, or a mixture thereof.

Substantially any type of neutralized suitable enteric coating material could be used in order to coat the benzimidazole substrate, including but not limited to, cellulose acetate phthalate (CAP); hydroxypropyl methylcellulose phthalate (HPMCP); polyvinyl acetate phthalate; cellulose acetate trimellitate; poly((methacrylic acid, methyl methacrylate)1:1) (Eudragit L100™), poly((methacrylic acid, ethyl acrylate)1:1) (Eudragit L30D-55) or Eudragit L100-55™, (poly(methacrylic acid, methyl methacrylate)1:2) Eudragit™, hypromellose acetate succinate (HPMCAS), sodium alginate, and alginic acid or mixtures thereof.

As used herein, the term "neutralized enteric coating material" refers to enteric coating material which has been at least partially neutralized by reaction with an alkalizing agent. Suitable alkalizing agents for neutralizing the enteric polymer include, but are not limited, to amino alcohols such as methanolamine, monoethanol amine, propanolamine and alkylene diamines such as methylene diamine, ethylene diamine, propylene diamine, and ammonia solution such as ammonium hydroxide, basic ammonium salts, arginine, lysine and any other pharmaceutically acceptable amino compound bases, or a combination thereof.

Preferably, the enteric coating material is at least about 60% neutralized, more preferably the enteric coating material is at least about 80% neutralized, and most preferably the enteric coating material is at least about 95% neutralized.

The enteric coating is optionally prepared in an organic solvent, such as, for example, acetone, ethanol or isopropanol, or a combination thereof; such as a mixture of ethanol and water (30/70 or 40/60); or a mixture of isopropyl alcohol and ethanol.

The enteric coating optionally contains at least one of a plasticizer (such, as for example, a citric acid ester or a phthalic acid ester), a surfactant (such as, for example, polysorbate 80 or sodium lauryl sulfate), a glidant (such as, for example, talc or titanium dioxide), a coloring agent and a polishing agent.

The method for applying the enteric coating material to the substrate can vary. Substantially any coating method can be used, such as pan coating or fluidized bed coating, with the solution of the enteric coat chosen.

A preferred embodiment of the formulation of the present invention is presented in Example 1 below. Residual akalinizing agent in the coating was analyzed as described in Examples 2 and 3, respectively.

The following specific examples illustrate various aspects of the compositions of the present invention, and are not intended to be limiting in any way. Specific reference is made to Omeprazole for the purposes of description only and without intending to be limiting.

EXAMPLES

Example 1: Delayed Release Tablets, 20 mg OTC Formulation

| Ingredients | Pharmaceutical function | Amount mg/tablet | Percent/ tablet |
|---|---|---|---|
| Active constituent | | | |
| Omeprazole USP | Active | 20.00 | 6.51 |
| Core | | | |
| Lactose monohydrate NF | Filler | 203.00 | 66.12 |
| Sodium starch glycolate NF | disintegrant | 10.00 | 3.25 |
| Sodium stearate NF | alkalinizing agent | 10.00 | 3.25 |
| Sodium stearyl fumarate NF | lubricant | 7.00 | 2.28 |
| Coating | | | |
| Hypromellose acetate succinate NF | enteric coating polymer | 32.00 | 10.42 |
| Triethyl citrate NF | plasticizer | 4.50 | 1.47 |
| Sodium lauryl sulfate NF | wetting agent | 0.50 | 0.16 |
| Talc USP | Glidant | 8.14 | 2.65 |
| Strong ammonium solution NF | alkalinizing agent | NA* | — |
| Monoethanolamine NF | alkalinizing agent | 1.00 | 0.33 |
| Sepisperse AP 3527 | coloring agent | 10.80 | 3.52 |
| Carnauba wax NF | polishing agent | 0.06 | 0.02 |
| Purified water | Solvent | NA* | — |
| Total weight | | 307.00 | Ca 100 |

*strong ammonium solution is used as a volatile alkalizing agent which is evaporated during the coating process.

Preparation of the substrate: Omeprazole was thoroughly mixed with lactose, sodium starch glycolate, sodium stearate and sodium stearyl fumarate. The mixture was then compressed into tablets weighing 250 mg each. The tablets were then transferred into a conventional coating pan and coated with the enteric coating, prepared as described below.

Preparation of Enteric Coating

Coating A: triethyl citrate was dissolved in water, sodium lauryl sulfate was then added to this solution, HPMCAS and talc were dispersed in this solution, such that the concentration of HPMCAS was about 7% weight per volume. Monoethanolamine was added to this dispersion. Ammonia in a 25% solution was added to adjust the pH value in a range of from about 7 to about pH 9. The pigment was then added to the enteric coating dispersion.

Coating B: Triethyl citrate was dissolved in a mixture of isopropyl alcohol and alcohol, sodium lauryl sulfate was then added to this solution, HPMCAS and talc were dispersed in this solution, such that the concentration of HPMCAS was about 6% weight per volume. Ammonia in a 25% solution was added to adjust the pH value in a range of from about 7 to about pH 9. The pigment was then added to the enteric coating dispersion. The tablet cores were then transferred into a conventional coating pan and coated with the enteric coating layer.

Coating C: Triethyl citrate was dissolved in water to form an aqueous solution; sodium lauryl sulfate was then added to this aqueous solution. HPMCAS, colloidal silicon dioxide and talc were dispersed in this solution, such that the concentration of HPMCAS was about 7% weight per volume. Ammonia in a 25% solution was added to adjust the pH value of the coating dispersion in a range of from about 7 to about pH 9.

Coating D: Triethyl citrate was dissolved in water to form an aqueous solution; sodium lauryl sulfate was then added to this aqueous solution. HPMCAS, talc, and monoethanolamine were dispersed in this solution. Ammonia in a 25% solution was added to adjust the pH value of the coating dispersion in a range of from about 7 to about pH 9.

Example 2: Omeprazole Delayed Release Tablets 20 mg—Determination of Ammonia

Samples were stored at room temperature prior to analysis.

The samples were analyzed according to Standard Methods for Examination of Water and Waste Water, Ed. 19, 1995, Method 4500-$NH_3$ F (phenate method). The samples were prepared in triplicate by adding 30 ml HPLC grade water to one tablet, shaking overnight on an inverting shaker, followed by centrifugation at 4000 rpm for 15 minutes. This solution was filtered through 2 layers of glass fiber cartridge (GFC) filters and analyzed according to the above mentioned method. Quantitation was performed using a calibration curve prepared from solutions of $NH_4Cl$ in water in the concentration range of 0.05 µg/mL to 1.0 µg/mL $NH_3$. The uncoated tablets served as a control sample for the analysis of the coated tablets.

Results are presented in Table 1.

TABLE 1

| Lab no. | Batch No. (based on Example 1) | $NH_3$ mg/tablet |
| --- | --- | --- |
| 3789 | BO415 (coated) | 0.011; 0.07; 0.011 Mean 0.010 |
| 3980 | BO425 (coated) | 0.09; 0.010; 0.010 Mean 0.010 |
| 3981 | BO515 (coated) | 0.010; 0.012; 0.011 Mean 0.011 |

Example 3: Omeprazole Delayed Release Tablet 20 mg—Determination of Residual Monoethanolamine Samples were stored at room temperature prior to analysis.
Materials

| Dansyl chloride | Across 1158500 |
| --- | --- |
| Sodium hydrogen carbonate | Merck 106329 |
| Acetone | J.T. Baker 9002 |
| Acetonitrile | J.T. Baker 9017 |
| Sodium hydroxide | J.T. Baker 3722 |
| Water HPLC grade | Milli-Q in-house |
| Monoethanolamine | Analyst sample 5015 |
| Hydrochloric acid | Riedel de Haen 30721 |

Equipment

| Test tubes PP 50 ml | |
| --- | --- |
| Laboratory glassware Class A | |
| GFC filter paper 12.5 cm | Whatman 1822-125 |
| Shaker | Heidolf |
| Centrifuge capable of maintaining 4000 rpm | |

HPLC instrument and conditions

| Apparatus: | Agilent 1100 with variable wavelength detector and autosampler and Chemstation Rev A 10.01 software |
| --- | --- |
| Column: | Symmetry C 18 4.6 × 150 mm, 3.5µ |
| Injection volume: | 10 µL |
| Flow rate: | 1.0 mL/min |
| Detection: | 254 nm |
| Column temperature: | ambient |
| Run time: | 10 minutes |
| Retention time of MEA derivative: | ~5.3 minutes |

Solutions

Hydrochloric acid 4 N was prepared by mixing 83.3 mL of concentrated hydrochloric acid (specific gravity 1.19, 37%) with 200 mL water in a 250 mL volumetric flask. The volume was made up with water.

Dilute hydrochloric acid was prepared by adding 1.2 mL hydrochloric acid (specific gravity 1.19, 37%) to a 1 L volumetric flask containing about 500 mL water, diluting to volume with water and mixing well.

Mobile phase was prepared by mixing 600 mL of water with 400 mL acetonitrile, mixing well and sonicating to degas.

0.2% dansyl chloride was prepared by weighing accurately about 100 mg dansyl chloride in a 50 mL volumetric flask and diluting with acetone.

0.1 M sodium hydrogen carbonate was prepared by weighing about 840 mg of sodium hydrogen carbonate into a 100 mL volumetric flask, diluting with water to give a pH of 9.0.

Monoethanolamine standard stock solution (1000 µg/mL) was prepared in duplicate by weighing accurately about 100 mg of monoethanolamine into a 100 ml volumetric flask, dissolving and diluting with water.

Monoethanolamine intermediate standard stock solution (100 µg/mL) was prepared by adding 5.0 mL standard stock solution to a 50 mL volumetric flask with dilute hydrochloric acid.

Monoethanolamine working standard solution (10 µg/mL) was prepared from intermediate standard stock solution by adding 5.0 mL to a 50 mL volumetric flask with dilute hydrochloric acid.

Sample Preparation

Samples were prepared in duplicate. One tablet was placed per 50 mL conical test tube and 50 mL of water added. Test tubes were placed on an inverting shaker at speed 6 for 2-3 hours, until disintegration of the tablets, then acidified by adding 200 µL of 4 N HCl. Test tubes were centrifuged for 15 minutes at 4000 rpm and filtered through Whatman GFC.

Derivatization Reaction

The procedure was performed on water as control and on all standards and samples, directly in autosampler vials.

100 µL of water, standard or sample solution was mixed with 200 µL 0.2% dansyl chloride solution. 400 µL 0.1 M sodium hydrogen carbonate and 400 µL acetone were added. The vials were closed, mixed and heated for 20 minutes in a water bath at 60° C. The contents of the vials were cooled to room temperature and injected into the HPLC system.

Results are presented in Table 2.

TABLE 2

| Lab no. | Sample name | Monoethanolamine mg/tablet |
|---|---|---|
| 3789 | BO415 | 0.77 (% RSD = 6.0) |
| 3980 | BO425 | 0.730; 0.681 Mean 0.71 |
| 3981 | BO515 | 0.822; 0.755 Mean 0.79 |
| 5273 | BO615 | 0.908; 0.780 Mean 0.84 |

Example 4: Suitability of Test Method for Determination of Residual Monoethanolamine In order to evaluate the suitability of the method as described above, the method was evaluated for specificity, linearity, precision (system and method) and recovery.

In order to demonstrate the specificity, the following samples and solutions were analyzed: a sample blank (water); a standard containing 10 µg/mL monoethanolamine that had undergone the derivatization procedure; omeprazole tablets, prepared without the use of monoethanolamine, prepared according to the test method; and water.

Specificity

As shown in FIGS. 1 to 6, no interfering peaks at the retention time of monoethanolamine were recorded in the chromatograms of the blank sample, water, or the tablet without monoethanolamine.

Linearity

The linearity of the method was demonstrated in the range of from 1 to 50 µg/mL, monoethanolamine, corresponding to 0.05 to 2.5 mg/tablet. Results are presented in Table 3.

TABLE 3

| Concentration (µg/mL) | Peak area mAU*s | % difference |
|---|---|---|
| 0/96 | 7.4978E±00 | 43.7 |
| 1.92 | 1.5817E±01 | 10.9 |
| 4.81 | 4.4112E±01 | −2.5 |
| 9.62 | 9.2365E±01 | −6.0 |
| 19.24 | 2.0443±02 | −0.4 |
| 48.10 | 5.2640±02 | 0.3 |
| correlation | 0.99982 | |
| square correlation | 0.99963 | |
| slope | 1.1074E+01 | |
| intercept | −7.8104E+00 | −7.6 |

Precision

The precision of the method was evaluated by replicate injections of a standard containing a nominal 10 µg/mL monoethanolamine derivatized according to the test method (system precision) and by preparing a sample of omeprazole tablets in 6 independent replicates according to the test method (method precision).

The system precision results as presented in Table 4 show that good precision was obtained for the peak areas as well as for the retention times.

TABLE 4

| Replicate | Retention time (mm) | Peak areas mAU*s |
|---|---|---|
| 1 | 5.291 | 9.0628E+01 |
| 2 | 5.286 | 8.9055E+01 |
| 3 | 5.283 | 9.1252E+01 |
| 4 | 5.283 | 8.8879E+01 |
| 5 | 5.762 | 8.9296E+01 |
| 6 | 5.225 | 9.0930E+01 |
| Mean | 5.272 | 9.0007E+01 |
| % RSD | 0.5 | 1.2 |

Method precision was performed using 6 preparations of omeprazole tablets (analyst sample 3789). Results were calculated against a standard containing 9.62 µg/mL monothenaolamine with an average peak area of 9.5519E+01 mAU*s, using the following formula:

$$mg/tablet = \frac{area\ smp \times Cst \times 50}{area\ st \times 1000}$$

area smp=monoethanolamine peak area in sample chromatogram area st=average peak area of standard "10 µg/mL"

cst=standard concentration in µg/mL

50=sample extraction volume (mL)

1000=conversion factor of µg to mg

Figure 5:
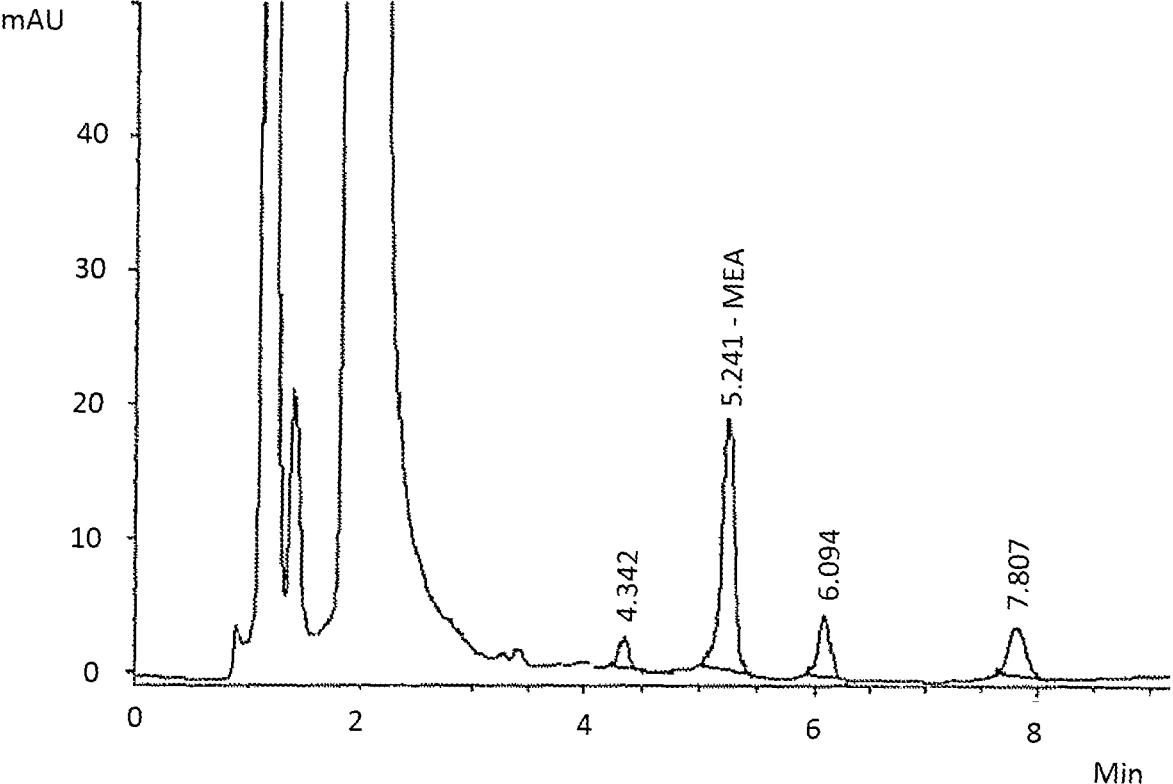

A representative chromatogram is presented in FIG. 5.

Method precision data and results are presented in Table 5.

TABLE 5

| Analyst no. and replicate | Sample name | MEA peak area mAU*s | Concentration of MEA in sample solution (µg/mL) | MEA in tablets mg/tablet |
|---|---|---|---|---|
| 3789-1 | coated | 1.4518E+0.2 | 14.6 | 0.731 |
| 3789-2 | BO415 | 1.6711E+0.2 | 16.8 | 0.842 |
| 3789-3 | | 1.4151E+0.2 | 14.3 | 0.713 |
| 3789-4 | | 1.5385E+0.2 | 15.5 | 0.775 |
| 3789-5 | | 1.5710E+0.2 | 15.8 | 0.791 |
| 3789-6 | | 1.5804E+0.2 | 15.9 | 0.796 |
| MEAN | | | | 0.774 |
| % RSD | | | | 6.0 |

Recovery

The recovery of the method was demonstrated by spiking control (no monoethanolamine) and monoethanolamine-containing omeprazole tablets with three levels of monoethanolamine.

Omeprazole tablets containing monoethanolamine (sample 3789, batch B0415) were spiked at the 0.1% w/w level in triplicate. Omeprazole control tablets (no MEA) were spiked at three levels with 0.15, 0.3 and 0.9 mg/tablet, corresponding to 0.05, 0.1 and 0.3% w/w. The test was performed by transferring the tablets to 50 mL test tubes, adding suitable volumes of a solution of 1000 µg/mL MEA, followed by 50 ml of water and preparation according to the method described above.

Results as presented in Tables 6 and 7 show good recovery results, within generally accepted limits for residue analysis. Recovery results were calculated against a standard containing 9.62 μg/mL MEA with an average peak area of 9.5519E+01 mAU*s. The recovery results in the tablets containing MEA were calculated as follows:

$$\% \ recovery = \frac{mg/tablet \ found \times 100}{average \ mg/tablet(unspiked) + mg/tablet \ added}$$

Figure 6:
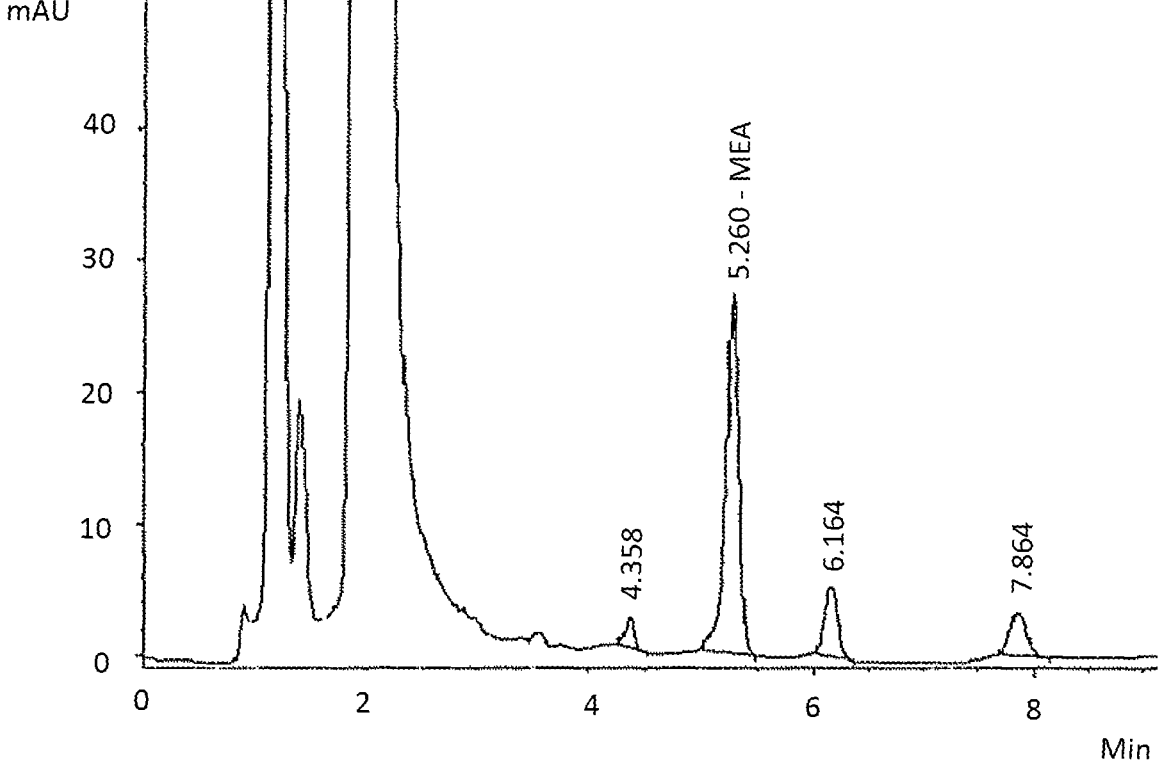

A representative chromatogram of omeprazole tablets (analyst sample 3789 Batch B0415) spiked with MEA is presented in FIG. 6.

Standard and Sample Solution Stability

During the method development, stock solution stability was demonstrated for 48 hours at room temperature. In addition, it was found that the MEA derivative is stable in autosampler vials at room temperature for at least 48 hours, because the response of the MEA derivative did not change upon reinjection.

Calculation of monoethanol amine and residual monoethanol amine in the coating.

These calculations show the weight percent of monoethanol amine and residual monoethanol amine in the coating of the omeprazole tablet formulation of Example 1. These calculations show that the weight percent of monoethanol amine is at least 1.195% of the coating.

TABLE 6

| Analyst No. and replicate | Sample name | MEA peak area (mAu*s) | Spiking level in mg/tablet | Concentration of MEA in sample solution (μg/mL) | MEA in tablets | % recovery |
|---|---|---|---|---|---|---|
| 5274-1 | omeprazole | 0.0000E+00 | | 0.0 | 0.000 | |
| 5274-2 | 20 mg | 0.0000E+00 | | 0.0 | 0.000 | |
| 5274-3 | uncoated 100605 | 0.0000E+00 | | 0.0 | 0.000 | |
| Mean | | | | | 0.000 | |
| 5274-1 | omeprazole | 2.4417E+0.1 | 0.144 | 2.46 | 0.123 | 85.5 |
| 5274-2 | 20 mg | 2.4339E+01 | | 2.45 | 0.123 | 85.2 |
| 5274-3 | uncoated 100605 | 2.4966E+01 | | 2.51 | 0.126 | 87.4 |
| Mean | | | | | 0.124 | 86.0 |
| % RSD | | | | | 1.4 | 1.4 |
| 5274-1 + 0.1% | omeprazole | 4.9693E+01 | 0.289 | 5.00 | 0.252 | 87.2 |
| 5274-2 + 0.1% | 20 mg | 5.1115E+01 | | 5.15 | 0.259 | 89.7 |
| 5274-3 + 0.1% | uncoated 100605 | 5.1356E+01 | | 5.17 | 0.260 | 90.1 |
| Mean | | | | | 0.257 | 89.0 |
| % RSD | | | | | 1.8 | 1.8 |
| 5274-1 + 0.3% | Omeprazole | 1.845E+02 | 0.962 | 18.59 | 0.948 | 98.5 |
| 5274-2 + 0.3% | 20 mg | 1.8919E+02 | | 19.05 | 0.972 | 101.0 |
| 5274-3 + 0.3% | uncoated 100605 | 1.8982E+02 | | 19.12 | 0.975 | 101.4 |
| Mean | | | | | 0.965 | 100.3 |
| % RSD | | | | | 1.5 | 1.5 |

TABLE 7

| Analyst No. and replicate | Sample name | MEA peak area mAU*s | Spiking level mg/tablet | Concentration of MEA in sample solution μg/mL | MEA in tablet mg/tablet | % recovery |
|---|---|---|---|---|---|---|
| 3789-1 | coated | 1.4518E+02 | | 14.6 | 0.731 | |
| 3789-2 | BO415 | 1.6711E+02 | | 16.8 | 0.842 | |
| 3789-3 | | 1.4151E+02 | | 14.3 | 0.713 | |
| Mean | | | | | 0.762 | |
| % RSD | | | | | 9.7 | |
| 3789-1 + 0.1% | coated | 2.1507E+0.2 | 0.289 | 21.721.773.8 | 1.083 | 107.6 |
| 3789-2 + 0.1% | B0415 | 2.1576E+0.2 | | | 1.086 | 107.9 |
| 3789-3 + 0.1% | | 2.3641E+0.2 | | | 1.1190 | 118.2 |
| Mean | | | | | 1.120 | 111.2 |
| % RSD | | | | | 5.5 | 5.5 |

TABLE 8

| | | | based on Example 1: |
|---|---|---|---|
| Ingredients | Amount mg/tablet | Percent/ tablet | Percent/coating |
| Coating of delayed release tablet | | | |
| Hypromellose acetate succinate NF | 32.00 | 10.42 | 32/57 × 100 = 56.14% |
| Triethyl citrate NF | 4.50 | 1.47 | 4.5/57 × 100 = 7.89% |
| Sodium lauryl sulfate NF | 0.50 | 0.16 | 0.5/57 × 100 = 0.88% |
| Talc USP | 8.14 | 2.65 | 8.14/57 × 100 = 14.28% |
| Strong ammonium solution NF | NA* | — | — |
| Monoethanolamine NF | 1.00 | 0.33 | 1/57 × 100 = 1.75% |
| Sepisperse AP 3527 | 10.80 | 3.52 | 10.8/57 × 100 = 18.95% |
| Carnauba wax NF | 0.06 | 0.02 | 0.06/57 × 100 = 0.11% |
| Purified water | NA* | — | — |
| Total coating | 57.0 | | 100% |

*strong ammonium solution is used as a volatile alkalizing agent which is evaporated during the coating process.

TABLE 9A

| | | | based on Table 2: | |
|---|---|---|---|---|
| Lab no. | Sample name | Monoethanolamine mg/tablet | Percent monoethanol amine in the coating | |
| 3789 | BO415 | 0.77 (% RSD = 6.0) | 0.77/57 × 100 = 1.35% | |
| 3980 | BO425 | 0.730; 0.681 Mean 0.71 | 0.73/57 × 100 = 1.28% 0.681/57 × 100 = 1.195% | |
| 3981 | BO515 | 0.822; 0.755 Mean 0.79 | 0.822/57 × 100 = 1.44% 0.755/57 × 100 = 1.325% | |
| 5273 | BO615 | 0.908; 0.780 Mean 0.84 | 0.908/57 × 100 = 1.59% 0.780/57 × 100 = 1.368% | |

TABLE 9B

| | | | | based on Table 5: | | |
|---|---|---|---|---|---|---|
| Analyst no. and replicate | Sample name | MEA peak area mAU*s | Concentration of MEA in sample solution (ug/mL) | MEA in tablets mg/tablet | Percent MEA in the coating | |
| 3789-1 | coated | 1.4518E+0.2 | 14.6 | 0.731 | 0.731/57 × 100 = 1.282% | |
| 3789-2 | BO4 15 | 1.6711E+0.2 | 16.8 | 0.842 | 0.842/57 × 100 = 1.477% | |
| 3789-3 | | 1.4151E+0.2 | 14.3 | 0.713 | 0.713/57 × 100 = 1.251% | |
| 3789-4 | | 1.5385E+0.2 | 15.5 | 0.775 | 0.775/57 × 100 = 1.360% | |
| 3789-5 | | 1.5710E+0.2 | 15.8 | 0.791 | 0.791/57 × 100 = 1.388% | |
| 3789-6 | | 1.5804E+0.2 | 15.9 | 0.796 | 0.796/57 × 100 = 1.396%. | |

Example 5: Omeprazole Delayed Release Tablets 20 mg—Determination of Final pH of Enteric Coating Enteric coated omeprazole tablets were prepared according to the composition of Example 1 (Batch #B0425). The enteric coating was prepared in aqueous dispersion, and the pH value of the coating dispersion was adjusted to the range from about 7 to about pH 9 by a combination of monoethanolamine and concentrated ammonia solution. The ammonia solution evaporated during the coating process.

The pH of the coating layer following evaporation of the ammonia solution was measured in the following test solutions:

1. Purified water (pH 5.9 at 22° C.), obtained from MILI Q system; and
2. 1% buffer solution of Intestinal Fluid NF (pH 6.9 at 22° C.) using potassium dihydrogenphosphate (lot #B36148 purchased from Baker), and sodium hydroxide (lot #B452998549 from Merck), with no pancreatin added.

For each test solution, three coated tablets were split and the core was removed by washing using purified water. The resulting film coats were then transferred into a vial containing 30 ml test solution, and stirred for 2 hours with a magnetic stirrer at 1000 rpm. The pH of the medium was determined.

It was found that in purified water, the coating films partially disintegrated and partially dissolved. The pH value of the medium was found to be 5.4.

In intestinal fluid, the coating films were fully disintegrated and fully dissolved (except for talc and the coloring powder of Sepisperse). The pH value of the medium was found to be 5.3. Hence, it is shown that the polymer retains its acidic properties and thus provides an acidic reaction.

Since the pH of the coating solution was initially basic, it can be concluded that the change in pH occurs due to evaporation of ammonia solution, causing the polymer, hydroxypropyl methylcellulose acetate succinate (HPMCAS) to revert to its acid form, having enteric properties. The acidic form of HPMCAS can be soluble in water only through ionization of all free acidic groups in an aqueous medium with pH values above 5.5. This is in fact the reason that the polymer is characterized as an enteric polymer. While the native pH value of pure HPMCAS aqueous dispersion is about 4.5, the pH value of about 5.3 found using the composition of the present invention may be due to the presence of residual monoethanolamine, which is used a second alkalizing agent for neutralization of HPMCAS.

The present study shows that when the entering coating polymer is placed in purified water as test medium, a partial dissolution of the polymer first takes place, which continues for as long as the pH of the medium remains basic. Once the pH of the medium reaches an acidic value of about 5.4, dissolution of the polymer stops and the polymer disintegrates. In diluted neutral buffer solution-1% simulated intestinal fluid, on the other hand, an acidic pH was achieved only after full polymer dissolution.

The temporarily neutralized HPMCAS coating prepared using a high concentration of ammonia during the coating process provides an enteric film coat surrounding the omeprazole-containing cores which can withstand pH values of up to about 5. This can provide the active material with an appropriate protection while passim through the stomach even if the pH values of gastric fluid are elevated.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An omeprazole delayed release tablet consisting of:
a core consisting of omeprazole, lactose, sodium starch glycolate, sodium stearate, and sodium stearyl fumarate; and an enteric coating over the core consisting of hydroxypropyl methyl cellulose (HPMC) acetate succinate, triethyl citrate, sodium lauryl sulfate, talc, monoethanol amine, a coloring agent and less than 500 ppm of residual ammonium hydroxide;
wherein said monoethanol amine is prepared from an aqueous solution and is present in the coating in an amount of 1.195 weight %, 1.251 weight %, 1.28 weight %, 1.282 weight %, 1.325 weight %, 1.35 weight %, 1.360 weight %, 1.368 weight %, 1.388 weight %, 1.396 weight %, 1.44 weight %, 1.477 weight %, 1.59 weight %, or 1.75 weight % to reduce residual ammonium hydroxide in said tablet to a lower amount for toxicity/safety reasons.

2. An omeprazole delayed release tablet consisting of:
a core and an enteric coating over the core,
wherein the core consists of about: 20 mg omeprazole, 203 mg lactose monohydrate, 10 mg sodium starch glycolate, 10 mg sodium stearate, and 7 mg sodium stearyl fumarate,
wherein the enteric coating consists of hydroxypropyl methyl cellulose (HPMC) acetate succinate, triethyl citrate, sodium lauryl sulfate, talc, monoethanol amine, a coloring agent and less than 500 ppm of residual ammonium hydroxide;
wherein said monoethanol amine is prepared from an aqueous solution and is present in the coating in an amount of 1.195 weight %, 1.251 weight %, 1.28 weight %, 1.282 weight %, 1.325 weight %, 1.35 weight %, 1.360 weight %, 1.368 weight %, 1.388 weight %, 1.396 weight %, 1.44 weight %, 1.477 weight %, 1.59 weight %, or 1.75 weight % to reduce residual ammonium hydroxide in said tablet to a lower amount for toxicity/safety reasons.

3. An omeprazole delayed release tablet consisting of:
a core and an enteric coating over the core,
wherein the core consists of about: 8 weight % omeprazole, 81.2 weight % lactose monohydrate, 4 weight % sodium starch glycolate, 4 weight % sodium stearate, and 2.8 weight % sodium stearyl fumarate by weight percent of the core,
wherein the enteric coating consists of hydroxypropyl methyl cellulose (HPMC) acetate succinate, triethyl citrate, sodium lauryl sulfate, talc, monoethanol amine, a coloring agent and less than 500 ppm of residual ammonium hydroxide by weight percent of the enteric coating;
wherein said monoethanol amine is prepared from an aqueous solution and is present in the coating in an amount of 1.195 weight %, 1.251 weight %, 1.28 weight %, 1.282 weight %, 1.325 weight %, 1.35 weight %, 1.360 weight %, 1.368 weight %, 1.388 weight %, 1.396 weight %, 1.44 weight %, 1.477 weight %, 1.59 weight %, or 1.75 weight % to reduce residual ammonium hydroxide in said tablet to a lower amount for toxicity/safety reasons.

4. The omeprazole delayed release tablet of claim 1, wherein the omeprazole is present in the core in an amount of 20 mg.

5. The omeprazole delayed release tablet of claim 1, wherein the omeprazole is present in the core in an amount of about 8 weight %.

6. The omeprazole delayed release tablet of claim 2, wherein the HPMC acetate succinate is present in the coating in an amount of 32 mg, the triethyl citrate is present in the coating in an amount of 4.5 mg, the sodium lauryl sulfate is present in the coating in an amount of 0.5 mg, the talc is present in the coating in an amount of 8.14 mg, and the coloring agent is present in the coating in an amount of 10.8 mg.

7. The omeprazole delayed release tablet of claim 3, wherein the HPMC acetate succinate is present in an amount of 56.14 weight % of the coating, the triethyl citrate is present in an amount of 7.89 weight % of the coating, the sodium lauryl sulfate is present in an amount of 0.88 weight % of the coating, the talc is present in an amount of 14.28 weight % of the coating, and the coloring agent is present in an amount of 18.95 weight % of the coating.

8. The omeprazole delayed release tablet of claim 1, wherein the monoethanol amine is present in the coating in an amount of 1.195 weight %.

9. The omeprazole delayed release tablet of claim 1, wherein the monoethanol amine is present in the coating in an amount of 1.75 weight %.

10. The omeprazole delayed release tablet of claim 2, wherein the monoethanol amine is present in the coating in an amount of 1.195 weight %.

11. The omeprazole delayed release tablet of claim 2, wherein the monoethanol amine is present in the coating in an amount of 1.75 weight %.

12. The omeprazole delayed release tablet of claim 3, wherein the monoethanol amine is present in the coating in an amount of 1.195 weight %.

13. The omeprazole delayed release tablet of claim 3, wherein the monoethanol amine is present in the coating in an amount of 1.75 weight %.

* * * * *